United States Patent [19]
Bryant et al.

[11] Patent Number: 5,248,300
[45] Date of Patent: Sep. 28, 1993

[54] AMBULATORY INFUSION SYSTEM WITH SPRING-PRESSURIZED RESERVOIR

[75] Inventors: Peter L. Bryant, Libertyville; Lois L. Caron, McHenry; Nicolaos A. Drivas, Des Plaines; Richard W. Grabenkort, Barrington; William L. Rudzena, McHenry, all of Ill.

[73] Assignee: Abbott Laboratories, Abbott Park, Ill.

[21] Appl. No.: 808,420

[22] Filed: Dec. 16, 1991

[51] Int. Cl.$^5$ .............................. A61M 5/20
[52] U.S. Cl. ................... 604/134; 222/95; 222/103; 128/DIG. 12; 604/131
[58] Field of Search ............. 604/130-132, 604/140, 134; 128/DIG. 12; 222/95, 103, 105, 92

[56] References Cited

U.S. PATENT DOCUMENTS

| | | | |
|---|---|---|---|
| 2,397,257 | 3/1946 | Goland et al. | 604/131 |
| 3,151,616 | 10/1964 | Selfon | 604/131 |
| 3,494,509 | 2/1970 | McGuire | 222/95 |
| 4,090,514 | 5/1978 | Hinck et al. | 222/95 |
| 4,140,117 | 2/1979 | Buckles et al. | 604/132 |
| 4,337,769 | 7/1982 | Olson | 604/131 |
| 4,379,453 | 4/1983 | Baron | 222/95 |
| 4,447,232 | 5/1984 | Sealfon et al. | 604/134 |
| 4,539,005 | 9/1985 | Greenblatt | 222/95 |
| 4,627,554 | 12/1986 | Leibinsohn | 222/103 |
| 4,722,732 | 2/1988 | Martin | 604/248 |
| 4,741,736 | 5/1988 | Brown | 604/131 |
| 4,781,689 | 11/1988 | Sealfon et al. | 604/134 |
| 5,045,064 | 9/1991 | Idriss | 604/132 |
| 5,059,174 | 10/1991 | Vaillancourt | 604/131 |
| 5,106,374 | 4/1992 | Apperson et al. | 604/140 |
| 5,122,116 | 6/1992 | Kriesel et al. | 604/132 |

FOREIGN PATENT DOCUMENTS 1159246  6/1958  France ................ 222/103

Primary Examiner—Randall L. Green
Assistant Examiner—Gina M. Gualtieri
Attorney, Agent, or Firm—Thomas M. Breininger

[57] ABSTRACT

An ambulatory infusion system includes a spring-pressurized reservoir to facilitate portable use of the system. The system includes a liquid-filled flexible container, and a pair of opposed platens between which the flexible container is removably positionable. Energy-storing, clip-like biasing springs act against the platens to urge them toward each other, thereby effecting pressurization of the liquid within the container. A tubing set of the system preferably includes a non-adjustable flow restrictor, which may be sized for relatively low flow rates to permit the system to be used for catheter patency maintenance.

12 Claims, 3 Drawing Sheets

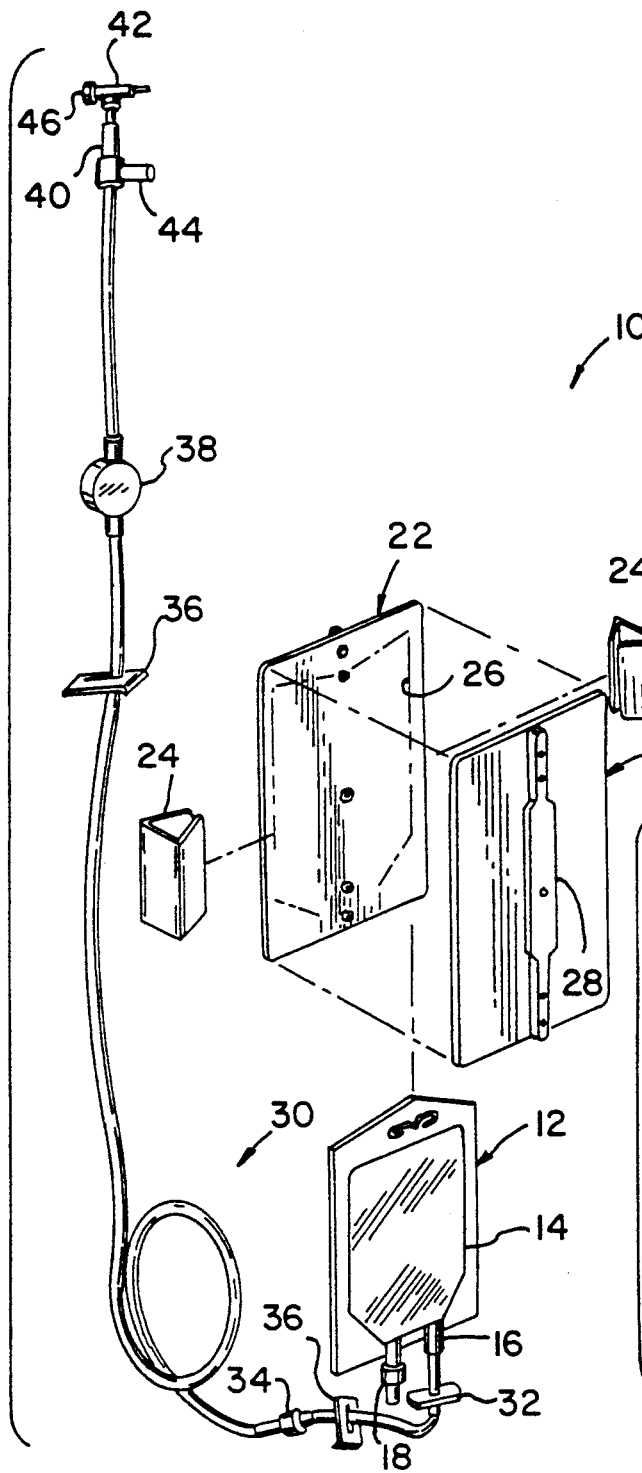
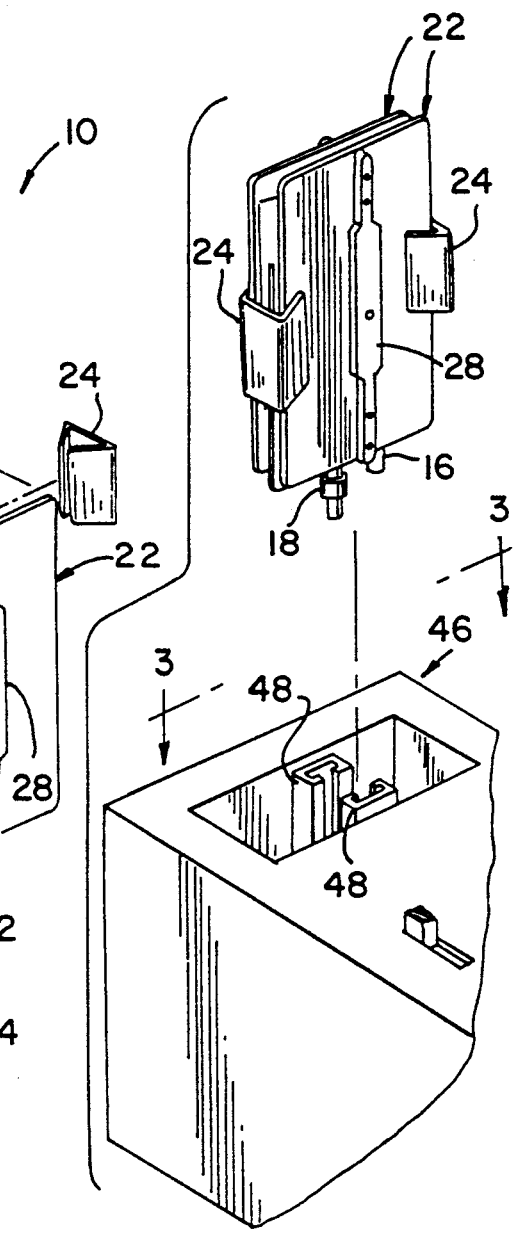

AMBULATORY INFUSION SYSTEM WITH SPRING-PRESSURIZED RESERVOIR

TECHNICAL FIELD

The present invention relates generally to infusion systems for patient care, and more particularly to an ambulatory infusion system including a portable, spring-pressurized reservoir arrangement, which system can be operated at relatively low flow rates to maintain the patency of an associated patient catheter, or for administering medicament or nutritional solutions.

BACKGROUND OF THE INVENTION

Patient therapy which requires use of an indwelling vein access device such as a catheter, ordinarily necessitates patency maintenance of the catheter to permit infusion of medicament, or nutritional solutions as required. Two procedures are typically employed for such patency maintenance.

The so-called SASH procedure includes administration of an anticoagulant heparin solution through a series of steps. Specifically, the indwelling catheter device is first flushed with a bolus dose of saline solution, followed by infusion of a medicament or nutritional solution. The catheter device is again flushed with a bolus dose of saline solution, and the device is thereafter filled with a concentrated solution of heparin. While this procedure is generally regarded as being effective to maintain catheter patency, the procedure can be time-consuming and costly. Additionally, the patient may experience some discomfort and a burning sensation attendant to administration of the heparin.

The second widely employed practice for maintaining catheter patency is generally referred to as the KVO procedure, i.e., keep vein open. This practice entails a substantially continuous infusion of a saline solution at flow rates on the order from about 1 ml per hour (as is typical with power-driven infusion pump devices) to 10 ml per hour (as is typical with gravity systems).

While KVO practice has distinct advantages over the above-described SASH procedure, the required continuous infusion of a saline solution ordinarily severely restricts the mobility of a patient. Gravity flow infusion devices ordinarily require that the patient be positioned in close proximity to an i.v. pole, while infusion pump devices typically are relatively heavy, and require connection to an associated power source.

The present invention relates to a highly portable infusion system which can be employed for KVO practice without restricting patient mobility, and which is further adaptable for infusion of medicament or nutritional solutions as may be required for patient care.

SUMMARY OF THE INVENTION

The present invention relates to an ambulatory infusion system including a spring-pressurized reservoir arrangement, which system is substantially self-contained and portable in use. The system includes a replaceable liquid container which holds a solution to be administered to a patient, and an associated arrangement of spring-biased platens which act to pressurize the solution in the liquid container for effecting substantially continuous administration of the solution over extended time periods. In accordance with the illustrated embodiment, the platens are configured to facilitate removable association with a separate power-driven opening apparatus, which apparatus can be operated to separate the platens for convenient replacement of the liquid container. Applications include low rate flushing to maintain catheter patency, oncology, and ambulatory antibiotic drug delivery.

In accordance with the illustrated embodiment, the liquid container of the present infusion system comprises a flexible, disposable container which functions as a reservoir and retains liquid for administration to a patient. For KVO practice, this liquid would ordinarily be a saline solution, with the container including a flow port through which the liquid is administered.

The present system further includes a self-powered arrangement for pressurizing the liquid container for use of the system. The construction includes a pair of cooperating, generally planar platens arranged in generally parallel spaced relationship to each other. The associated flexible liquid container is removably positionable between the opposed inner surfaces of the platens in a sandwich-like arrangement.

In accordance with the illustrated form, the construction further includes a pair of clip-like biasing springs which are fitted to the platens, and which are arranged to act against the outer surfaces thereof for biasing the platens toward each other to effect pressurization of the liquid in the flexible container. The biasing springs act as energy-storing devices for the construction, with the platens and biasing springs cooperating with the flexible liquid container to act as a spring-pressurized reservoir. This arrangement permits administration of the liquid from the flexible container over extended periods without impairing patient mobility.

In the preferred form, the present infusion system includes a tubing set joined in fluid communication with the flow port of the liquid container through which liquid is administered to the patient. Notably, the tubing set preferably includes a non-adjustable flow restrictor which controls flow of liquid from the container in accordance with a predetermined administration schedule. For use of the present system for KVO practice, a capillary flow restrictor is preferably employed in order to provide a relatively low flow rate to an associated catheter, thereby maintaining the patency thereof. As will be appreciated, the self-powered nature of the system, together with the non-adjustable capillary flow restrictor, facilitates consistent, reliable operation of the system in a self-regulating manner. By this arrangement, the system is capable of providing relatively low, steady stream flow rates on the order of 0.5 to 1 ml per hour for extended periods.

In accordance with the illustrated form, each of the platens is configured for cooperation with an associated power-driven opening apparatus by removable disposition of the spring-biased platens therein. The opening apparatus, which is intended for non-portable use such as in a pharmacy or the like, is operable to grip the cooperating platens, and effects separation of the platens away from each other in opposition to the biasing springs, thus facilitating replacement of the liquid container, as required. If desired, removable spacers can be employed to maintain the platens in spaced apart relationship prior to use of the infusion system. The spacers are removable for effecting pressurization of the liquid in the flexible container by the biasing springs acting on the platens. The spacers thus act to prevent pressurization of the liquid container prior to use of the system.

Other features and advantages of the present invention will become readily apparent from the following detailed description, the accompanying drawings, and the appended claims.

BRIEF DESCRIPTION OF THE DRAWINGS

FIG. 1 is an exploded perspective view of the ambulatory infusion system embodying the principles of the present invention;

FIG. 2 is a partially exploded, perspective view of a spring-pressurized reservoir of the present infusion system which is positionable in association with a power-driven opening apparatus;

DETAILED DESCRIPTION

Figure 3:
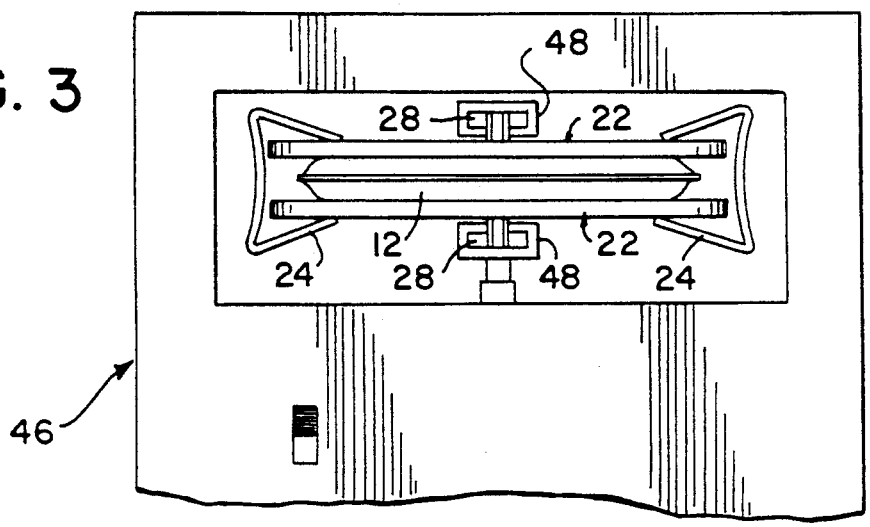
FIG. 3 is a view taken along lines 3—3 of FIG. 2.

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiment illustrated.

With reference to FIG. 1, therein is illustrated an ambulatory infusion system 10 embodying the principals of the present invention. As will be further described, the present infusion system is particularly suited for providing relatively low flow rates of a solution, such as for KVO practice, with the system further being suited for administration of medicament or nutritional solutions, as required.

As shown in FIG. 1, the present infusion system includes a flexible and pliable liquid container 12 which retains the liquid for administration to a patient. The container 12 may be conventional in nature, such as the type of disposable, flexible container ordinarily used for storing and intravenously administering solutions. As such, the container 12 includes a liquid retaining portion 14 defined inwardly of the outer periphery of the container, and includes a puncturable flow port 16 through which liquid flows from the container. In the preferred form, the container includes an additional reseal port 18, thus permitting introduction of a medication or the like into the solution within the container.

For use of the present system, the liquid container 12 is removably positionable in association with a spring-pressurizing arrangement which comprises a pair of generally rectangular opposed platens 22. Platens 22 are substantially rigid in construction to preclude significant deformation of the platens during use of the system.

Energy for operation of the system is provided by a pair of clip-like, generally C-shaped biasing springs 24 which are fitted to respective opposite side edges of the opposed platens 22. The biasing springs 24 are arranged to act against outer surfaces of the platens 22, thereby biasing the platens toward each other to effect pressurization of liquid container 12 when the liquid container is positioned between the inner surfaces of the generally parallel, spaced apart platens. Pressurization of the liquid within the container 12 to a pressure on the order of 10-20 psi can be readily achieved.

As shown in FIG. 1, the desired cooperation of the platens 22 with the container 12 for effecting pressurization thereof is promoted by configuring the inner surfaces of the platens to be generally complementary to the liquid retaining portion 14 of a container. To this end, at least one, and preferably both of the platens 22 define a recess 26 at the respective inner surfaces thereof, which recess is generally complementary to liquid retaining portion 14 of the container.

As noted above, the present infusion system is particularly suited for ambulatory patient use, in some instances for extended time periods. It is thus contemplated that the system first be prepared for use, such as in the pharmacy of a healthcare facility, with the system thereafter used by the patient with little or no further manipulation required by the patient during use.

To this end, each of the platens 22 preferably includes a generally elongated opening element 28 on the outer surface thereof. Each of these opening elements preferably has at least a portion of a generally T-shaped cross-section, with the elements being configured for slidable, removable disposition in an opening apparatus, as will be further described, for effecting preparation of the infusion system for use.

As shown in FIG. 1, the present infusion system preferably includes a tubing set, generally designated 30, through which liquid is administered from liquid container 12 to a patient. In the illustrated embodiment, the tubing set includes a piercing pin 32 which can be removably inserted into the puncturable flow port 16 of the container 12. A luer lock connector 34 is provided downstream of the piercing pin 32, with slide clamps 36 preferably provided for controlling flow through the tubing set. The tubing set preferably includes an air-elimination filter 38, of conventional construction, to assure that any air present in the tubing set does not reach the associated catheter.

In order to promote ambulatory patient use of the present system, the tubing set 30 preferably includes a non-adjustable flow restrictor 40, which promotes administration of liquid from the system in accordance with a predetermined administration schedule. For KVO therapy, flow restrictor 40 preferably comprises a capillary flow restrictor, such as having a bore on the order of 0.0016 inches. The flow restrictor may be integral with a catheter connector 42 which can be releasably connected to an indwelling catheter. Substantially constant flow rates as low as 1 ml per hour can be reliably achieved with the present system.

In view of the relatively restricted flow through flow restrictor 40, priming of the tubing set 30 with liquid from container 12 is facilitated by the preferred provision of a selectively, manually operable bypass valve 44 positioned in parallel flow relationship with the flow restrictor. Opening of bypass valve 44, which can be provided in any variety of forms, acts to bypass the restrictor 40, thereby permitting relatively unrestricted fluid flow through the tubing set for priming the set with liquid. After priming, bypass valve 44 is closed, so that subsequent flow passes through restrictor 40 to connector 42. The bypass valve may be separate from, or integrated with, flow restrictor 40.

Figure 6:
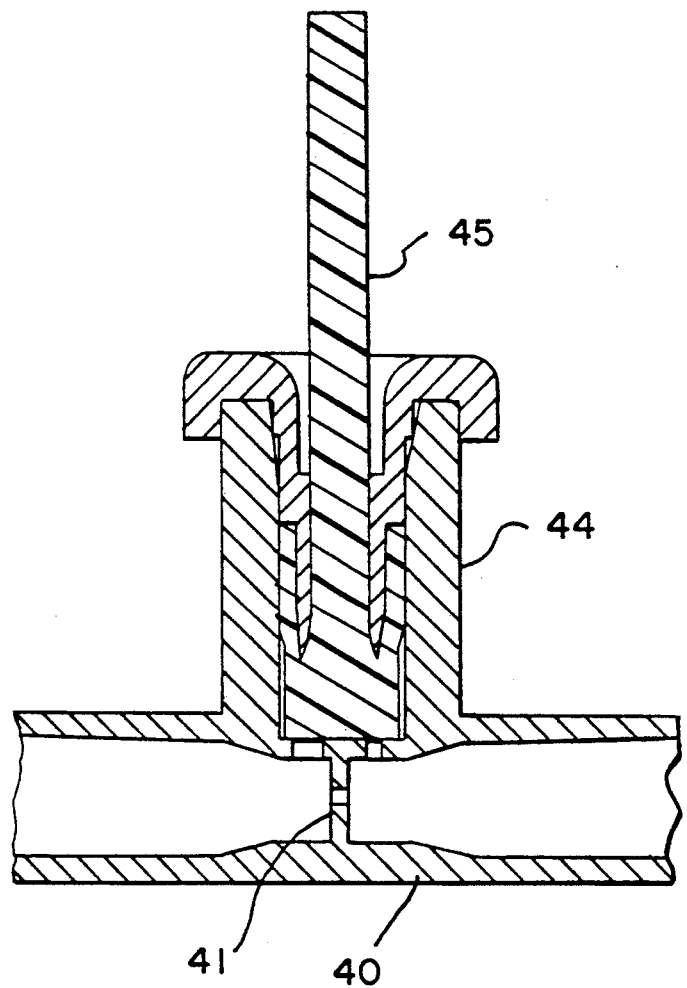
FIG. 6 is a cross-sectional view of a flow restrictor and bypass valve of the present system.

An exemplary bypass construction is shown in FIG. 6, with flow restrictor 40 shown as comprising a member 41 defining a flow-restricting hole, and with bypass valve 44 comprising an elastomeric valve member 45 which is selectively movable by pulling to open a relatively unrestricted flow passage bypassing member 41. As will be appreciated, a suitable bypass arrangement can be otherwise configured, such as comprising a rotary valve member, or other arrangement.

In the preferred form, catheter connector 42 of the tubing set includes a reseal port 46 positioned downstream of the flow restrictor 40 and bypass valve 44. The reseal port permits administration of a medicament to the patient through the associated catheter, with the liquid being administered through the tubing set desirably acting to thereafter flush the catheter. This assures that the complete dose of medicament is administered, and acts to preclude any undesired reaction between the medicament and any subsequently administered solution. By the preferred provision of bypass valve 44 together with flow restrictor 40, this flushing can be achieved at a relatively low flow rate with liquid flow through the restrictor, or at a relatively high flow rate with liquid flow through the bypass valve.

As noted, platens 22 preferably include external opening elements 28 to facilitate opening of the spring-biased platen for positioning flexible container 12 therebetween. For this purpose, an associated power-driven opening apparatus 46 is preferably employed. Apparatus 46 is intended for non-portable use, such as in a pharmacy or the like, with the apparatus including a pair of opposed gripping jaws 48 which are complementary to opening elements 28 on the platens 22. By this arrangement, the gripping jaws 48 of the apparatus 46 can be selectively operated and positioned for slidably, removably receiving the opening elements 28 of platens 22 therein. Operation of the apparatus 46 then effects opening and separation of the platens 22 away from each other, in opposition to biasing springs 24. In this manner, the liquid container 12 can be readily removably positioned in platens 22, for subsequent pressurization upon release of the platens 22.

Figure 4:
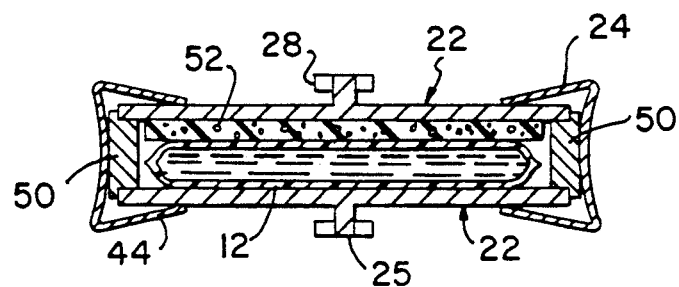
FIG. 4 is a cross-sectional view of the spring-pressurized reservoir of the present system, illustrating optional features thereof.
Figure 5:
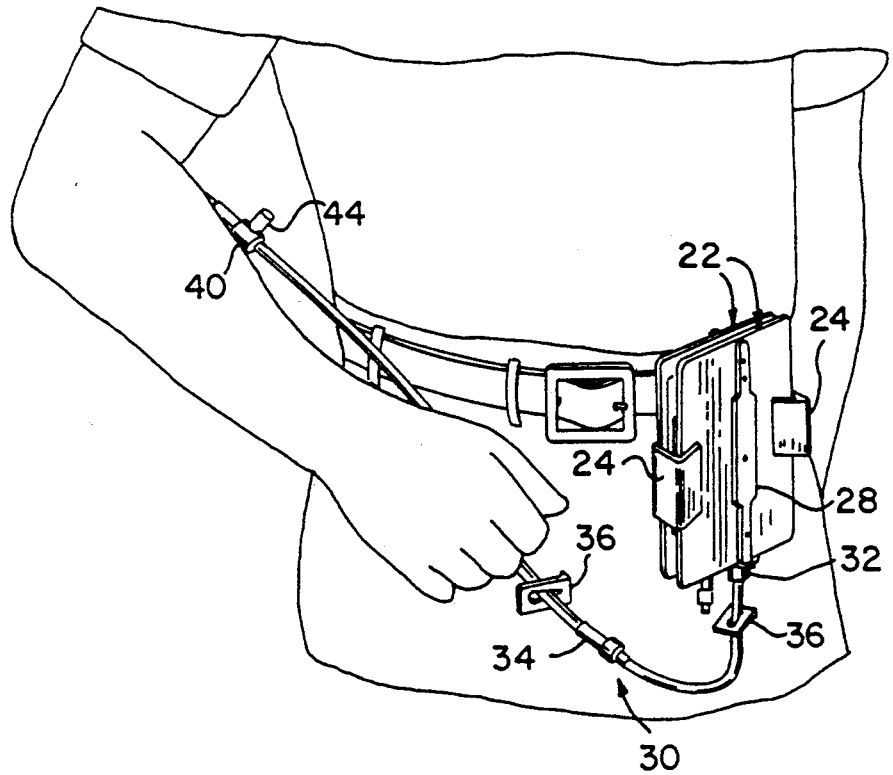
FIG. 5 illustrates the present infusion system in use by a patient.

With reference to FIG. 4, optional features of the present system are illustrated. If desired, a pair of spacers 50 can be optionally employed to maintain platens 22 in spaced apart relationship in opposition to biasing springs 24, prior to pressurization of the container 12. When it is desired to use the system, removal of spacers 50 permits the biasing springs 24 to bias and urge platens 22 toward each other for pressurizing the liquid container.

FIG. 4 further illustrates the provision of an optional flexible compression layer 52 positioned intermediate the liquid container 12 and the inner surface of one of the platens 22. Compression layer 52 may comprise suitable foam material, and is provided for conforming to irregularities exhibited by the liquid container 12, thereby promoting pressurization and flow of liquid from the container.

From the foregoing, it will be observed that numerous modifications and variations can be effected without departing from the true spirit and scope of the novel concept of the present invention. It is to be understood that no limitation with respect to the specific embodiment illustrated is intended or should be inferred. The disclosure is intended to cover by the appended claims all such modifications as fall within the scope of the claims.

What is claimed is:

1. An ambulatory infusion system, comprising:
   a flexible liquid container for retaining a liquid for administration to a patient, said container including a flow port through which liquid is administered; and
   means for pressurizing said liquid container comprising a pair of cooperating platen means between inner surfaces of which said liquid container is removably positionable, and means for biasing said platen means toward each other for effecting pressurization of liquid in said container,
   each of said platen means including opening means configured for removably cooperating with an associated opening means which effects separation of said platen means away from each other to facilitate replacement of said liquid container between said platen means, and
   removable spacer means positionable to maintain said platen means in spaced apart relationship prior to use of said infusion system, said spacer means being removable for effecting pressurization of liquid in said container by said biasing means acting on said platen means.

2. An ambulatory infusion system in accordance with claim 1, including
   a tubing set connectable in fluid communication with the flow port of said liquid container through which liquid is administered, said tubing set including non-adjustable flow restrictor means which controls the flow of liquid from said container in accordance with a predetermined administration schedule.

3. An anbulatory infusion system in accordance with claim 2, wherein
   said tubing set further includes air-elimination filter means for filtering air from liquid being administered from said liquid container.

4. An ambulatory infusion system in accordance with claim 2, wherein
   said tubing set further includes selectively operable bypass valve means positioned in parallel flow relationship with said flow restrictor means for selectively bypassing said restrictor means to facilitate priming with liquid from said liquid container.

5. An ambulatory infusion system in accordance with claim 4, wherein
   said tubing set further includes reseal port means downstream of said flow restrictor means and said bypass valve means to permit administration of a medicament to the patient through an associated catheter, with liquid being administered through the tubing set acting to thereafter flush the catheter.

6. An ambulatory infusion system in accordance with claim 1, including
   flexible compression means positioned intermediate said liquid container and the inner surface of one of said platen means, said compression means conforming to irregularities exhibited by said liquid container to promote pressurization and flow of liquid from the container.

7. An ambulatory infusion system, comprising:
   a flexible liquid container for retaining a liquid for administration to a patient, said container including a flow port through which liquid is administered;
   a tubing set connectable in fluid communication with the flow port of said liquid container through which liquid is administered to a patient through an associated catheter; and
   means for pressurizing said liquid container for effecting flow of liquid through said flow port and said tubing set, said pressurizing means comprising a pair of cooperating platen means arranged in generally parallel spaced apart relationship, with said liquid container removably positionable between inner surfaces thereof, said pressurizing means further comprising biasing spring means arranged to act against outer surfaces of said platen means for biasing said platen means toward each other to effect pressurization of liquid in said container, each of said platen means including opening mans configured for slidably, removably cooperating with an associated opening apparatus, whereby said apparatus acts on the opening means to effect separation of said platen means away from each other in opposition to said biasing spring means to facilitate replacement of said liquid container between said platen means, and removable spacer means positionable to maintain said platen means in spaced apart relationship prior to use of said infusion system, said spacer means being removable for effecting pressurization of the liquid in said container by said biasing means acting on said platen means.

8. An ambulatory infusion system in accordance with claim 7, wherein said tubing set includes air-elimination filter means for filtering air from liquid being administered from said liquid container, said tubing set further including capillary flow restrictor means which controls the flow of liquid from said container to provide a relatively low flow rate to an associated catheter to maintain the patency of the catheter.

9. An anbulatory infusion system in accordance with claim 7, wherein said tubing set includes flow-restrictor means and selectively operable bypass valve means positioned in parallel flow relationship with said flow restrictor means for selectively bypassing said restrictor means to facilitate priming with liquid from said liquid container.

10. An ambulatory infusion system in accordance with claim 9, wherein said tubing set further includes reseal port means downstream of said flow restrictor means and said bypass valve means to permit administration of a medicament to a patient through an associated catheter, with liquid being administered through the tubing set acting to thereafter flush the catheter.

11. An ambulatory infusion system in accordance with claim 7, including flexible compression means positioned intermediate said liquid container and an inner surface of one of said platen means, said compression means conforming to irregularities exhibited by said liquid container to promote pressurization and flow of liquid from the container.

12. An ambulatory infusion system in accordance with claim 7, wherein inner surfaces of said platen means are generally complementary to a liquid retaining portion of said container.

* * * * *

UNITED STATES PATENT AND TRADEMARK OFFICE
CERTIFICATE OF CORRECTION

PATENT NO. : 5,248,300
DATED : September 28, 1993
INVENTOR(S) : Peter L. Bryant; Lois L. Caron; Nicolaos A. Drivas; Richard W. Grabenkort; William L. Rudzena It is certified that error appears in the above-indentified patent and that said Letters Patent is hereby corrected as shown below:

Column 6, line 30: Replace "anbulatory" with --ambulatory--

Column 7, line 11: Replace "mans" with --means--

Column 8, line 3: Replace "anbulatory" with --ambulatory--

Signed and Sealed this

Twenty-ninth Day of March, 1994

Attest:

BRUCE LEHMAN

Attesting Officer     Commissioner of Patents and Trademarks